(12) United States Patent
Mohr et al.

(10) Patent No.: US 7,689,261 B2
(45) Date of Patent: Mar. 30, 2010

(54) CARDIAC DISPLAY METHODS AND APPARATUS

(75) Inventors: Kelly Ann Mohr, New Berlin, WI (US); Laurent Stefani, Paris (FR); Laurent Launay, Saint Remy les Chevreuse (FR); Helen Jane Thomson, Auckland (NZ)

(73) Assignee: General Electric Company, Schenectady, NY (US)

( * ) Notice: Subject to any disclaimer, the term of this patent is extended or adjusted under 35 U.S.C. 154(b) by 1010 days.

(21) Appl. No.: 10/722,973

(22) Filed: Nov. 26, 2003

(65) Prior Publication Data

US 2005/0113665 A1 May 26, 2005

(51) Int. Cl.
*A61B 5/05* (2006.01)

(52) U.S. Cl. .................. 600/407; 600/410; 600/416; 600/425; 600/430; 600/436; 378/8

(58) Field of Classification Search .............. 378/8; 600/407, 410

See application file for complete search history.

(56) References Cited

U.S. PATENT DOCUMENTS

| | | | |
|---|---|---|---|
| 4,425,922 A | 1/1984 | Conti et al. | |
| 5,274,549 A * | 12/1993 | Almasi | 600/526 |
| 5,316,004 A | 5/1994 | Chesney et al. | |
| 5,421,331 A * | 6/1995 | Devito et al. | 600/425 |
| 5,435,310 A * | 7/1995 | Sheehan et al. | 600/416 |
| 5,564,427 A | 10/1996 | Aso et al. | |
| 5,617,459 A * | 4/1997 | Makram-Ebeid et al. | 378/62 |
| 5,680,471 A * | 10/1997 | Kanebako et al. | 382/128 |
| 5,724,981 A | 3/1998 | Apple | |
| 5,876,347 A | 3/1999 | Chesney et al. | |
| 6,120,459 A | 9/2000 | Nitzan et al. | |
| 6,152,879 A | 11/2000 | Mohler | |
| 6,185,447 B1 * | 2/2001 | Alley et al. | 600/420 |
| 6,249,693 B1 * | 6/2001 | Cline et al. | 600/410 |
| 6,373,920 B1 * | 4/2002 | Hsieh | 378/98.11 |
| 6,438,403 B1 * | 8/2002 | Cline et al. | 600/410 |
| 6,447,453 B1 * | 9/2002 | Roundhill et al. | 600/443 |
| 6,493,571 B1 * | 12/2002 | Bis et al. | 600/420 |
| 6,496,560 B1 * | 12/2002 | Lin et al. | 378/62 |
| 6,511,436 B1 | 1/2003 | Asmar | |
| 6,628,743 B1 * | 9/2003 | Drummond et al. | 378/8 |

* cited by examiner

*Primary Examiner*—Brian Casler
*Assistant Examiner*—James Kish
(74) *Attorney, Agent, or Firm*—Armstrong Teasdale LLP (57) ABSTRACT

A method includes receiving a multi-phase axial cardiac dataset, receiving a selection of a phase from a user, when the received selection is systole, generating an endocardial volume of a left ventricle at an end systole phase without further user intervention, and when the received selection is diastole, generating an endocardial volume of the left ventricle at an end diastole phase without further user intervention.

18 Claims, 9 Drawing Sheets

Representation of delineation of the LV from surrounding anatomy via thresholding, edge detection, and region growing algorithms. This is done at both end diastole and end systole to segment the contrast from the ventricular walls and ventricular walls from the contrast.

Figure 1. Typical workflow for current methodologies used to calculate LV functional parameters.

Prior Art

Figure 2. New workflow for accurate non-invasive measurement of cardiac function using tomographic images

Short Axis View

Horizontal Long Axis View
(Four-Chamber View)

Ventricle Long Axis
(Two-Chamber View)

LV Inflow/Outflow Tract View

Figure 3. Representative Short Axis, Vertical Long Axis, Horizontal Long Axis, and Left Ventricle Inflow/Outflow Tract views from a cardiac CT Exam Figure 4. Representation of delineation of the LV from surrounding anatomy via thresholding, edge detection, and region growing algorithms. This is done at both end diastole and end systole to segment the contrast from the ventricular walls and ventricular walls from the contrast.

Figure 5. An optimal combination of advanced algorithms such as thresholding, morphological and connectivity tools, edge detection, and region growing are used to segment the contrast within the ventricle from the myocardium.

Figure 6. Examples of 3D models of the LV at both end systole and end diastole. By measuring the volume of these models, EDV, ESV, SV, EF, and CO are calculated.

Figure 7. Volume rendering of the LV contrast at both end diastole and end systole.

CARDIAC DISPLAY METHODS AND APPARATUS

BACKGROUND OF THE INVENTION

This invention relates generally to CT, PET, and MR examinations of the heart, and more specifically to methods and apparatus for automating image generation and review.

Accurate evaluation of the cardiac function, particularly left ventricular (LV) function (e.g., stroke volume, ventricular ejection fraction, regional wall motion) is useful in cardiac diagnosis, guiding patient therapy, determining prognosis, and following the course of a disease. LV function is also a useful component of any comprehensive cardiac diagnostic examination for stable coronary artery disease (e.g., stable angina) and acute cardiac syndromes (e.g., acute myocardial infarction and unstable angina). Measurement of ventricular function complements and supplements other cardiac diagnostic procedures such as cardiac catheterization and coronary artery imaging for vessel patency and myocardial perfusion. In patients with a variety of heart diseases, cardiac function has a better diagnostic and prognostic value than vessel patency. For instance, even if a patient has stenosed coronary arteries as in chronic, stable coronary artery disease, close to normal ventricular function at rest and exercise suggests an excellent prognosis. On the other hand, even with good coronaries and normal perfusion, depressed ventricular function indicates a poor prognosis.

There are several known methods to measure cardiac function including echocardiography (Ultrasound), radionuclide imaging (positron emission tomography (PET)), magnetic resonance (MR) imaging, and computed tomographic (CT) imaging. One disadvantage of the echocardiographic methods is that they are highly operator dependent.

Three-dimensional imaging techniques of the heart are now widely used in several modalities (such as CT, MR, and PET). The review of these 3D datasets by a radiologist usually involves the creation of 2D reformatted slices (also called oblique planes) in specific anatomical orientations. These views are defined according to the long axis of the heart, which is defined as the line that joins the apex of the heart to the center of the mitral valve plane. For example, a Short Axis (SA) plane is the orientation orthogonal to the long axis allowing the visualization of cardiac anatomical structure in a meaningful cardiac plane without any foreshortening or elongation distorting structures and allowing comparison with output created from other cardiac imaging modalities. A SA plane is a cross-sectional view of the left ventricle, which is the standard plane for viewing the functional parameters of the heart. This allows the physician to view the motion of the heart through systole to diastole.

A Horizontal Long Axis (HLA) is the plane defined by the long axis and the four chamber cut plane (approximately the Left to the Right cut plane relative to the patient) allowing the visualization of cardiac anatomical structures in a meaningful cardiac plane without any fore-shortening or elongation distorting structures and allowing comparison with output created from other cardiac imaging modalities. This view allows for a four-chamber view of the heart displaying both the atria and ventricles in one view allowing visualization of the tricuspid and mitral valves.

A Vertical Long Axis (VLA) is the plane orthogonal to the HLA and containing the Long axis, allowing the visualization of cardiac anatomical structures in a meaningful cardiac plane without any fore-shortening or elongation distorting structures and allowing comparison with output created from other cardiac imaging modalities. This view allows for a two-chamber view of the heart displaying both the atria and ventricle of the heart.

An Inflow/Outflow view of the Left Ventricle allows additional views contributing to analysis of cardiac morphology.

The orientation of the heart within the chest may vary from patient to patient, therefore the geometric orientations of these anatomical planes have variability and must be determined specifically for each case.

Moreover, to review efficiently a 3D cardiac dataset, there is a need to display simultaneously several anatomical orientations in different view ports for review, with the images being linked by a common 3D cursor. The configurations of the views on the screen can vary, according to the preference of each physician or according to a specific clinical task.

Known techniques involve manual determination of each of these planes on the screen. This is performed by manually orienting each oblique view, based on other views. Creating several views in different orientations can be very time consuming. Therefore, below are described methods and apparatus which address the above problems, in one embodiment, with a unified automated solution.

BRIEF SUMMARY OF THE INVENTION

In one aspect, a method includes receiving a multi-phase axial cardiac dataset, receiving a selection of a phase from a user, when the received selection is systole, generating an endocardial volume of a left ventricle at an end systole phase without further user intervention, and when the received selection is diastole, generating an endocardial volume of the left ventricle at an end diastole phase without further user intervention.

In another aspect, a medical imaging apparatus for generating views of a heart along anatomically useful planes is provided. The medical imaging apparatus includes an imaging system including a detector array, at least one radiation source, and a computer coupled to the detector array source, and a workstation coupled to the computer. The workstation is configured to receive a multi-phase axial cardiac dataset from the computer, receive a selection of a phase from a user, when the received selection is systole, generate an endocardial volume of a left ventricle at an end systole phase without further user intervention, and when the received selection is diastole, generate an endocardial volume of the left ventricle at an end diastole phase without further user intervention.

In still another aspect, a computer readable medium encoded with a program executable by a computer for generating views of a heart along anatomically useful planes is provided. The program is configured to instruct the computer to receive a multi-phase axial cardiac dataset, receive a selection of a phase, when the received selection is systole, generate an endocardial volume of a left ventricle at an end systole phase without further input, and when the received selection is diastole, generate an endocardial volume of the left ventricle at an end diastole phase without further input.

DETAILED DESCRIPTION OF THE INVENTION

In the PET radionuclide imaging methods (also known as radionuclide angiography), a blood pool is labeled with a radioisotope (such as technetium-99m) and scanned using a gamma camera with R wave (ECG) gating. Volume changes within the ventricular cavity are computed from the quantification of the count rate changes. Although the radionuclide method is considered the 'gold standard' for quantitative assessment of global ventricular function and is relatively operator independent, it provides limited assessment of regional ventricular wall motion.

In the MR imaging methods, tomographic sections of the heart are combined to reconstruct a 3D image. Due to intrinsic contrast between blood and myocardial tissue, a blood pool can be segmented from the adjacent tissue in sectional views and the total volumes are calculated in systole & diastole. Although no contrast is injected and no radiation is administered to the patient, scanning times are typically relatively long (e.g., 10 to 15 minutes) with a potential for artifacts and degradation of IQ due to patient movements, including respiration. However, MR may have some advantage in quantifying contraction velocity in different regions of the ventricular wall.

Assessment of ventricular function by CT imaging is performed by injecting a contrast agent into a blood pool and imaging the heart around the area of contrast concentration in the heart. Employing an ECG (R wave) trigger, cardiac scans are obtained over several cardiac cycles during a single breath hold (typically 20 to 30 seconds) and images are reconstructed to provide axial images at all phases of the cardiac cycle. As this exam can be completed within a single breath hold, respiratory artifacts are practically eliminated. In addition, the patency of the coronary artery can be evaluated using the same exam (same scan data) by using a different reconstruction algorithm.

Both the tomographic methods of MR and CT for ventricular function rely upon a segmentation of the endocardial surface as contour lines that separate the contrast-rich blood from the ventricular wall in axial images. This reliance upon the segmentation of the endocardial surface may introduce errors due to inaccurate contours or discontinuities in the contours. These methods are semi-automatic and require appreciable user interaction with the apparatus used for measuring the ventricular function (e.g., an Image Review station such as an Advantage Windows (AW) workstation commercially available from General Electric Medical Systems of Waukesha Wis. or a Console). These semi-automatic methods requiring appreciable user interaction are often time-consuming. Additionally, intra- and inter-operator variability might affect the reproducibility and repeatability of the measurements.

Figure 1:
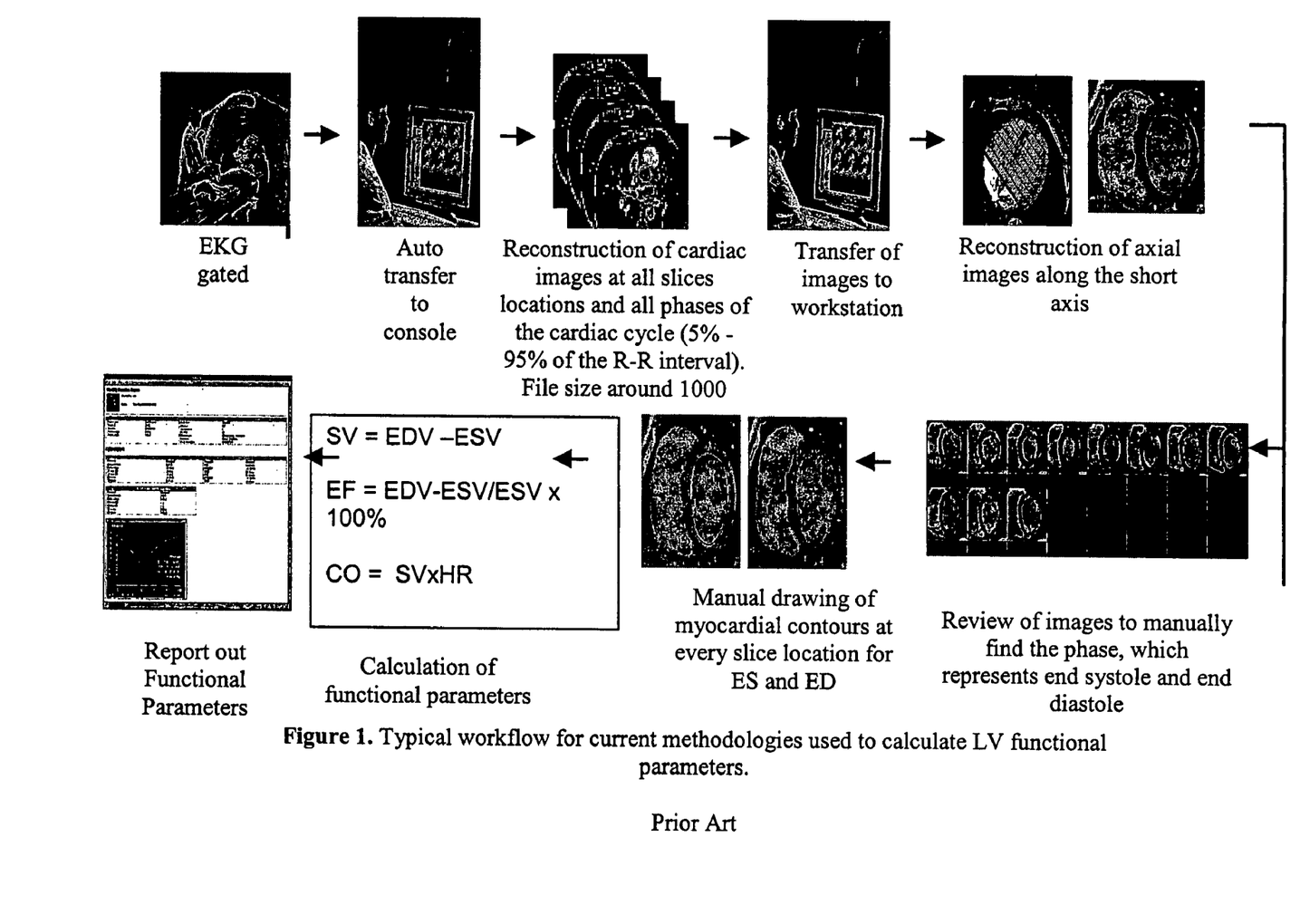
FIG. 1 illustrates a typical workflow for known methodologies used to calculate LV functional parameters.

FIG. 1 illustrates a typical workflow for known methodologies used to calculate LV functional parameters. In the known methods, computation of ventricular volume and the diagnostic parameters like ejection-fraction and cardiac output requires detection of myocardial boundaries. Correct and reproducible measurements of LV function, in terms of parameters such as the global and regional ejection fraction, require an accurate and reproducible method to delineate the left ventricle. Today, delineation can be accomplished manually or semi-automatically using different algorithms. Such manual tracking or semi automated boundary description is conducted by a trained clinician to locate and extract the LV contour. Although the reliability of the edited contour can be enhanced by introducing more skilled operators and a priori knowledge (such as location, shape, and intensity), manual tracking has two drawbacks. First, the obtained LV boundaries are biased—the tracked boundaries vary from individual to individual. Second, manual tracking is time-consuming.

Another drawback of the known methods is that the functional parameters are estimated by the assumption of an elliptical model for the left ventricle shape. This assumption can lead to important estimation errors. This problem has been addressed to some extent by the methods that use the more time consuming and manually intensive approach with the assumption of parallel projection geometry and by decomposing the object into several 2D slices that are reconstructed one at a time.

Figure 2:
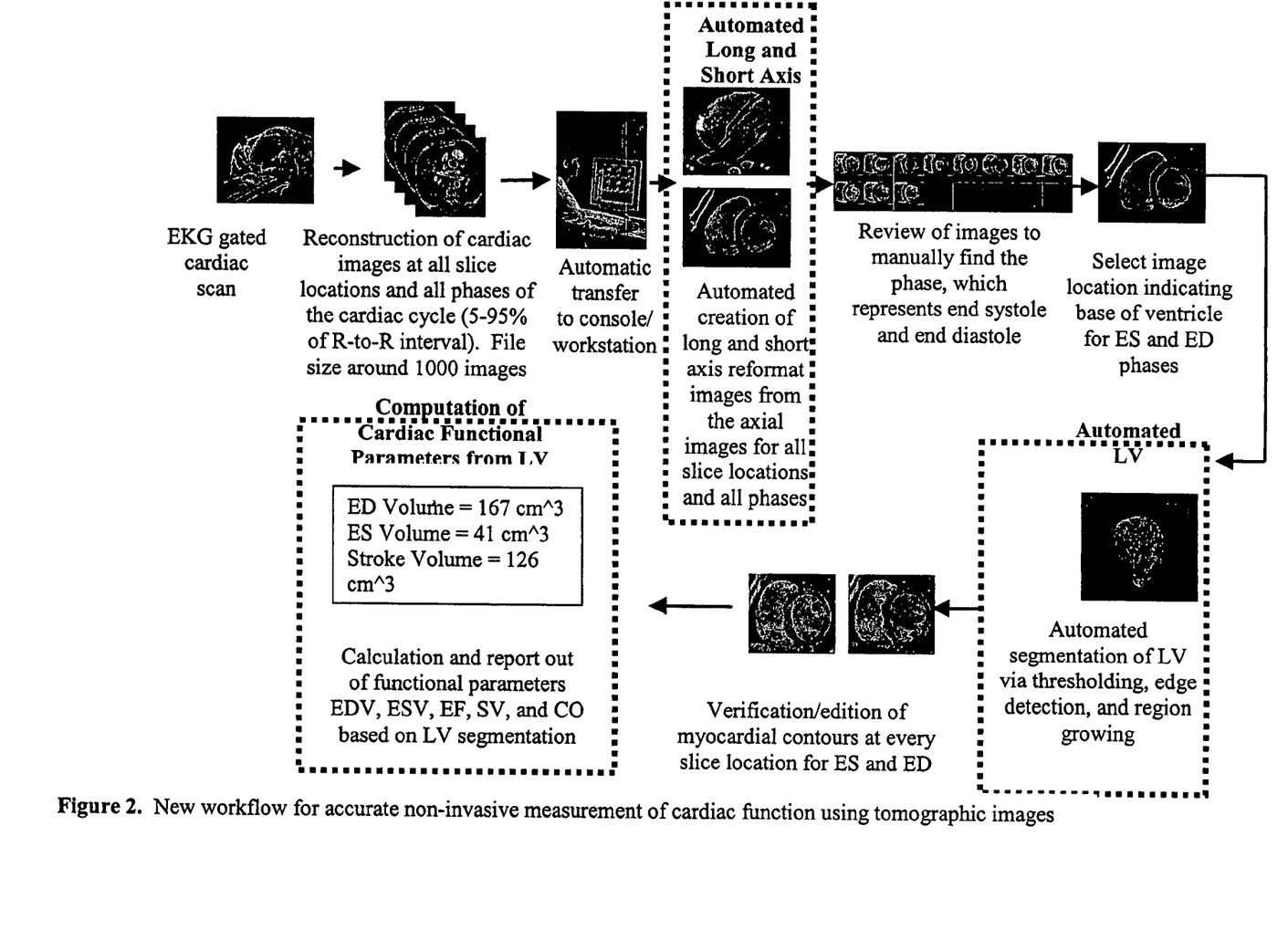
FIG. 2 illustrates a flow chart incorporating an analysis of cardiac scans acquired on an imaging scanner and transferred to a workstation.

FIG. 2 illustrates a flow chart incorporating an analysis of cardiac scans acquired on an imaging scanner (such as CT, MR, and nuclear/PET) and transferred to a console or an image workstation such as the Advantage Windows workstation. These images are processed by a series of new, automated methods, including Automated Short and Long Axis image creation, Automated LV Segmentation, and Calculation of Cardiac Function from LV Segmentation to produce a final report on cardiac functional parameters. Each of the new methods is described below.

The Automated Long and Short Axis Image Creation is as follows. This feature automatically determines the long and short axis orientation from a set of axial images. The user selects a multi-phase axial cardiac dataset and loads it into an 'Ejection Fraction' (EF) protocol running on an imaging workstation and/or console. Upon loading, the software algorithm processes the axial images to create long and short axis images. The herein described methods and apparatus provide a solution to very easily create a large collection of review layouts. Each review layout can be applied to any patient and provides automatically a set of oblique views showing the 3D cardiac dataset oriented to specific anatomical locations (SA, HLA, or VLA). A review layout then can be associated to a specific clinical task, or to the preferences of a specific physician.

A review layout is obtained by prescribing for each view its location on the screen and its anatomical orientation. The prescription is performed by using a specific data representation. This representation can for example, be coded

```
<layout>
    <Axial x=0 y=0>
    <Oblique x=512 y=0 orientation=SA />
    <Oblique x=0 y=512 orientation=VLA />
    <Oblique x=512 y=512 orientation=HLA />
</layout>
```

The above example creates an axial view in the upper left view port. The upper right view port holds an oblique view oriented along the Short Axis, and the lower left and right view ports hold images oriented along the vertical and horizontal long axis respectively.

A set of layouts can be associated to a specific clinical task. In one embodiment, a user interface allows the user to create and save their own layouts. The location of the view can be graphically prescribed on the screen, and the orientation can be chosen for each view from a list in a pull-down on-screen menu.

When a layout is applied to a specific 3D dataset, the orientation of each view is determined automatically by an algorithm that analyzes the 3D dataset.

The automatic orientation algorithm makes use of prior information on the anatomy of the heart, and, in one embodiment, includes three steps.

As a first step, a segmentation of the left cavity is performed on the volume whose cardiac EKG phase location is nearest to 75% of the R to R interval of the dataset. The algorithm produces a segmentation of the left cavity (atrium and ventricle) and the aorta as a connected component for this phase.

In a second step, the algorithm computes the axis of inertia, and the center of inertia of this segmented volume from the first step. This axis is a first estimate of the Long Axis, which will be refined in the third step.

In a third step, the algorithm uses a priori knowledge of the shape of the left ventricle to find two points along the Long Axis. The first point is the apex of the left ventricle. The algorithm determines this point as the right extremity (relative to the patient) of the previous segmentation. The second point should be proximal to the center of the mitral valve along the Long Axis. The center of inertia of the segmentation is proximal to this area (where the left ventricle locally looks like a cylinder along the Long Axis). To refine the position of this point, the algorithm intersects the segmentation of the left cavities with a plane orthogonal to the first estimate of the Long Axis and containing the center of inertia of the left cavities. The second point is the center of inertia of the intersection. The Long Axis is then defined as the axis connecting those 2 points in a line. The Short Axis is then determined from the Long Axis.

Figure 3:
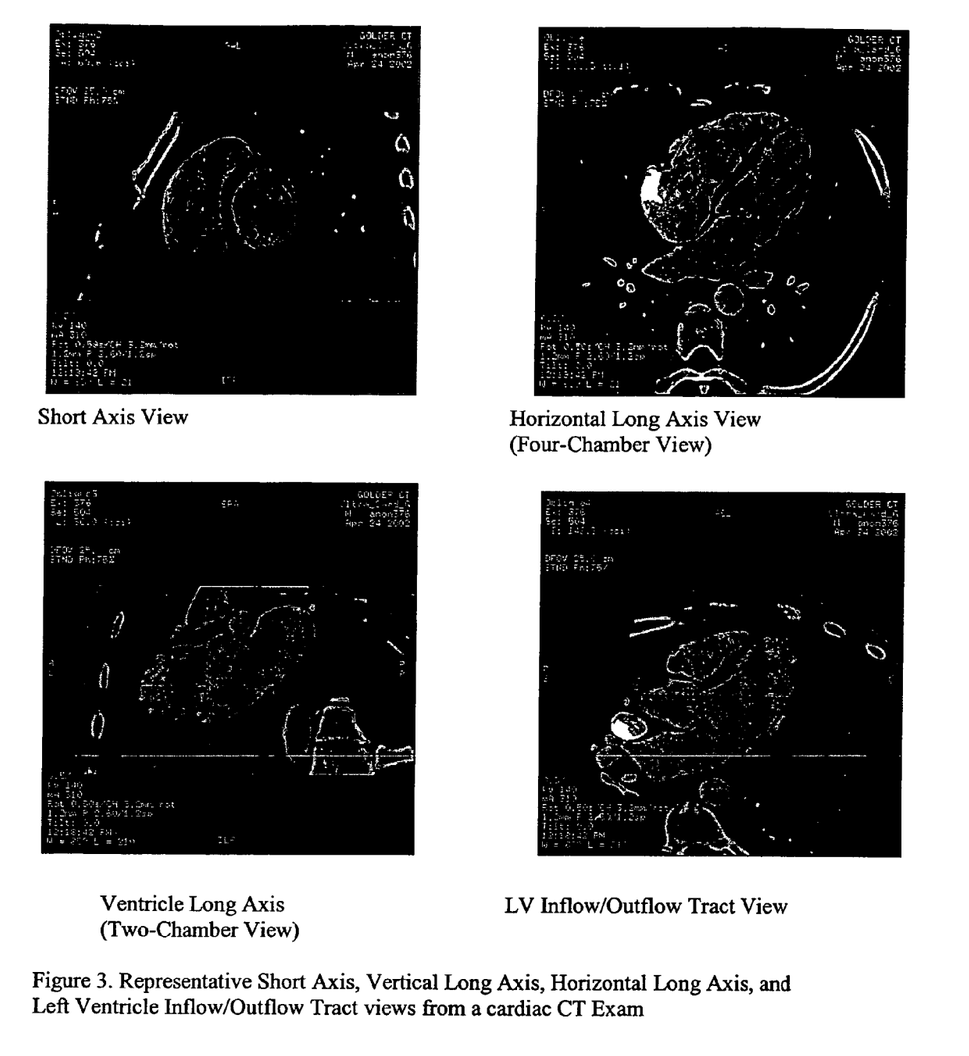
FIG. 3 illustrates representative Short Axis, Vertical Long Axis, Horizontal Long Axis, and Inflow/Outflow views from a cardiac CT Exam.

The resulting dataset can be used to automatically display images that can be associated to a specific clinical task. FIG. 3 illustrates representative Short Axis, Vertical Long Axis, Horizontal Long Axis, and Inflow/Outflow views from a cardiac CT Exam.

This methods described above are not limited to work with Computed tomography, but may be expanded to work additionally with datasets from Magnetic Resonance, Positron Emission Tomography, and other imaging modalities.

The Automated LV Segmentation is accomplished by using an optimal combination of thresholding, morphological and connectivity tools, and prior information on the anatomy, wherein the location of the center of the Left Ventricle is precisely and robustly determined. In the neighborhood around the location of the center of the LV, tracking algorithms such as edge detection and region growing tools separate the contrast in the left ventricle from the myocardial and papillary muscles (see e.g., J. H. C. Reiber, "Quantitative Analysis of Left Ventricular Function from Equilibrium Gated Blood Pool Scintigrams: an Overview of Computer Methods," *Eur J Nucl Med*, 10:97-110, 1985.; El O. Boudraa, J. J. Mallet, J. E. Besson, S. E. Bouyoucef, and J. Champier, "Left Ventricle Automated Detection Method in Gated Isotopic Ventriculography Using Fuzzy Clustering," *IEEE Trans. Med. Imaging*, vol. 12, no. 3, pp. 451-465, 1993.; M. Ekman, M. Lomsky, S. O. Stromblad, and S. Carlsson, "Closed-Line Integral Optimization Edge Detection Algorithm and Its Application in Equilibrium Radionuclide Angiocardiography," *J of Nucl Med*, vol. 36, no. 6, pp. 1014-1018, June 1995.; and M. Hosoba, H. Wani, M. Hiroe, and K. Kusakabe, "Clinical Validation of Fully-Automated Contour Detection for Gated Radionuclide Ventriculography with a Slant-Hole Collimator," *Eur J. Nucl Med*, 12:53-59, 1986. An endocardial volume of the LV is then created (see FIGS. 4 and 5) for both the ES and ED phases. End diastolic volume, end systolic volume, ejection fraction, stroke volume, and cardiac output are computed from these volumes. Table 1 includes descriptions of the above cardiac functional parameters.

TABLE 1

| Name | Abbreviation | Description | Equation | Units |
|---|---|---|---|---|
| End-Diastolic Volume | EDV | The volume of blood in the specified chamber at the end of the diastolic phase, when the chamber is at its fullest | Measured from volume rendering | ml |
| End-Systolic Volume | ESV | The volume of blood in the specified chamber at the end of the systolic phase, when the chamber contains the least volume | Measured from volume rendering | ml |
| Stroke Volume | SV | The amount of blood ejected from the left ventricle during systole | SV = EDV − ESV | L/beat |
| Ejection Fraction | EF | The percentage (%) of the end-diastolic volume ejected by the ventricle per beat; used as an indicator of overall cardiac function | EF = (EDV − ESV)/EDV × 100 or EF = (SV/EDV) × 100 | % |
| Cardiac Output | CO | The volume of blood pumped by the left ventricle in one minute | CO = SV × heart rate in beats per minute (bpm) | L/min. |

Figure 4:
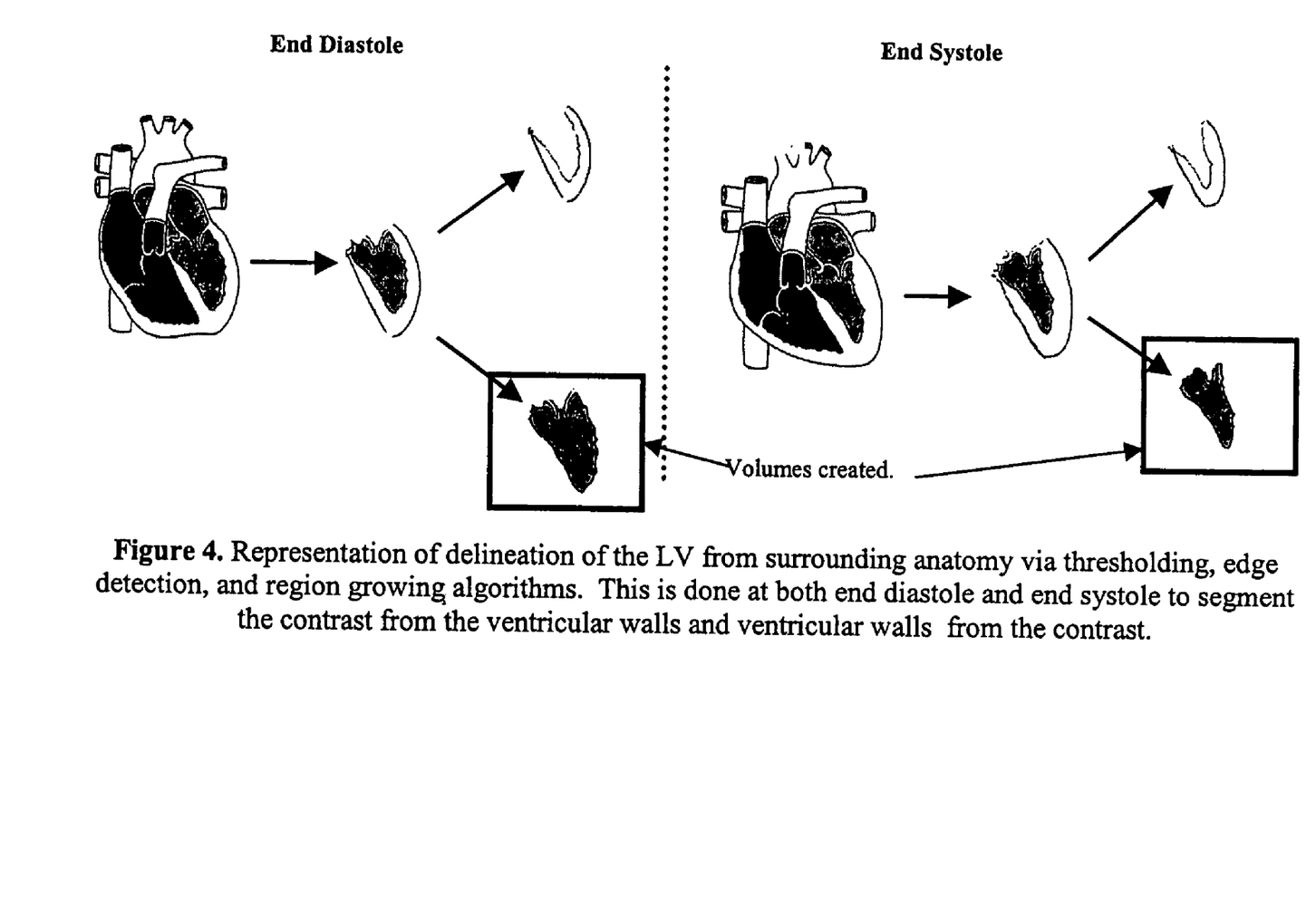
FIG. 4 illustrates the delineation of LV from surrounding anatomy.
Figure 5:
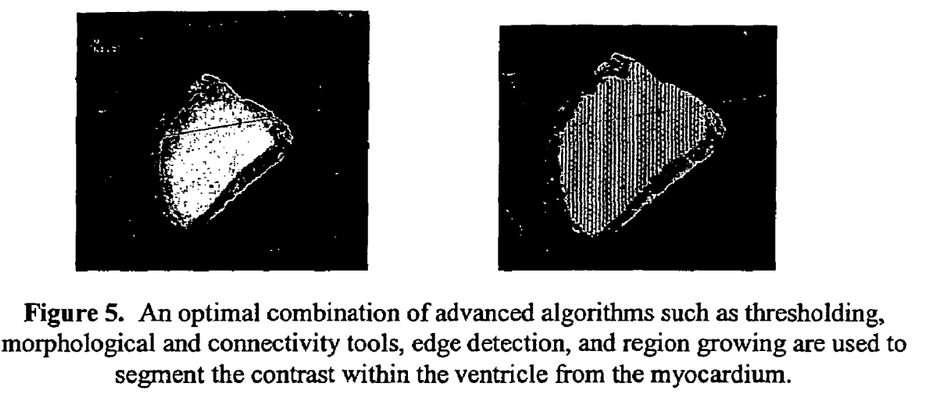
FIG. 5 illustrates an optimal combination of advanced algorithms such as thresholding, morphological and connectivity tools, edge detection, and region growing are used to segment the contrast within the ventricle from the myocardium.

As illustrated in FIG. 4, the volume rendering of the left ventricle eliminates the disadvantages of the known manual and semi-automated methods for volume calculations used today. The herein described automated volume rendering approach performs the reconstruction directly in the 3D space and considers the oblique projection geometry of the biplane acquisition system. FIG. 5 illustrates an optimal combination of advanced algorithms such as thresholding, morphological and connectivity tools, edge detection, and region growing are used to segment the contrast within the ventricle from the myocardium.

Figure 6:
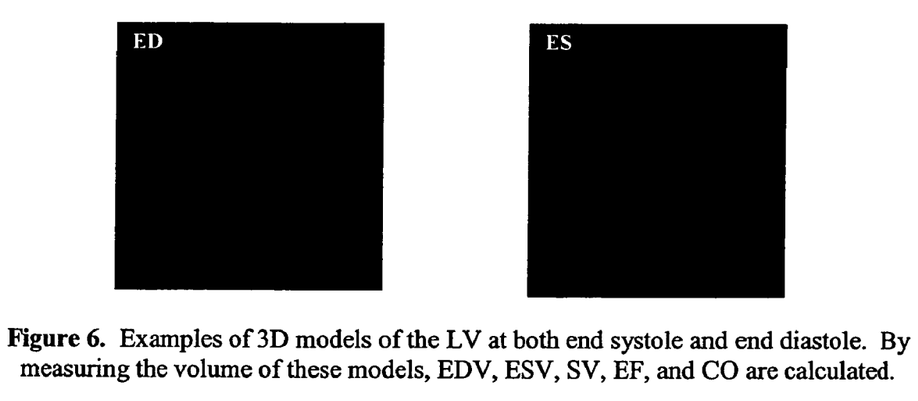
FIG. 6 illustrates examples of 3D models of the LV at both end systole and end diastole.
Figure 7:
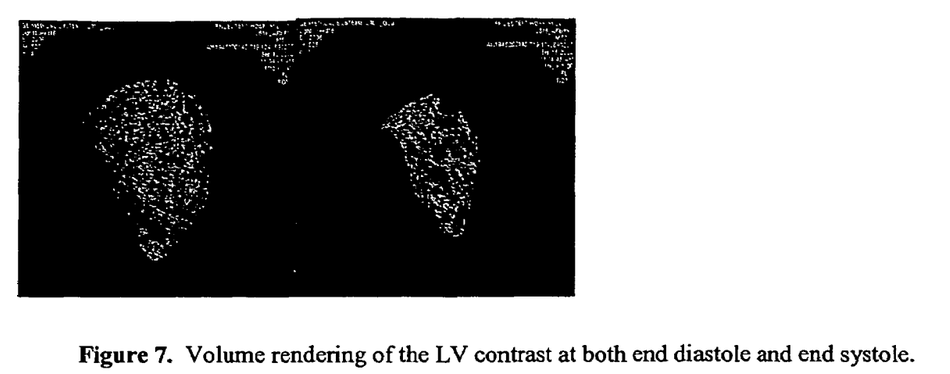
FIG. 7 illustrates Volume rendering of the LV contrast at both end diastole and end systole.

Using the volume rendering of the contrast contained within the ventricle at both end systole and end diastole, volumes at these phases are measured. Measured volumes represent only the blood pool and exclude the papillary muscles. The volume calculations do not smooth the contours of each slice. Along with excluding papillary muscles, this non-smoothing may improve accuracy of functional cardiac measurements. Using these volumes, cardiac functional parameters, namely, end diastolic and end systolic volumes, ejection fraction, stroke volume, and cardiac output are calculated. FIG. 6 illustrates examples of 3D models of the LV at both end systole and end diastole. By measuring the volume of these models, EDV, ESV, SV, EF, and CO are calculated. FIG. 7 illustrates Volume rendering of the LV contrast at both end diastole and end systole.

Figure 8:
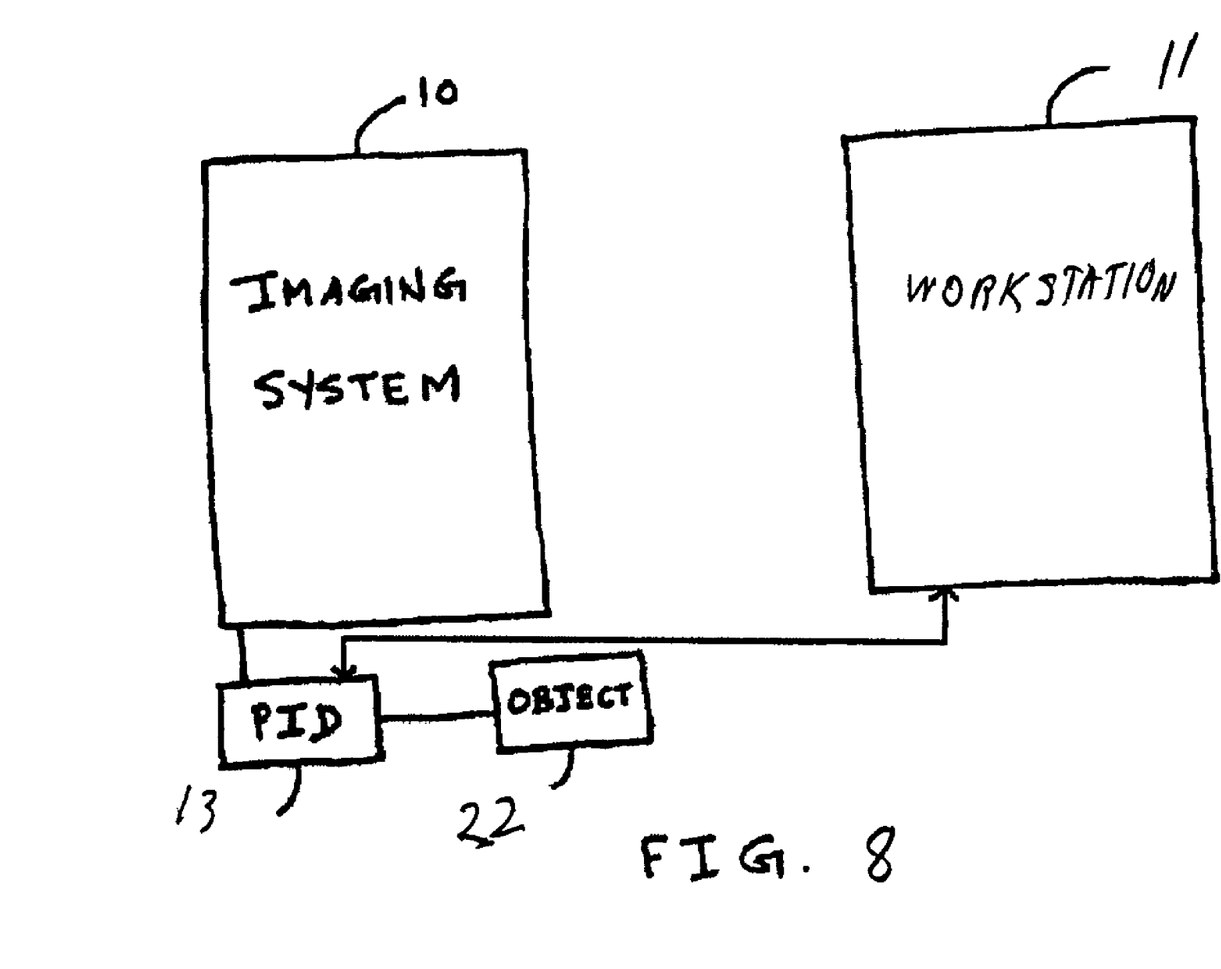
FIG. 8 is an embodiment of an imaging system in which systems and methods for improved workflow are implemented.

FIG. 8 is an embodiment of an imaging system 10 in which systems and methods for improved workflow are implemented. Examples of imaging system 10 include an ultrasound imaging system, magnetic resonance imaging (MRI)

system, single photon emission computed tomography (SPECT) imaging system, computed tomography (CT) imaging system, and positron emission tomography (PET) imaging system. A workstation 11 can be included within or located outside imaging system 10 and includes a computer. Imaging system 10 scans an object 22, such as a heart, a liver, or a lung, and generates original projection data. A Physiological information device (PID) 13 is coupled to workstation 11 and to object 22. An example of PID 13 includes an electrocardiograph that generates an electrocardiogram (EKG). PID 13 generates physiological cycle signals, such as EKG signals or respiratory signals, including a plurality of phases, such as cardiac phases or respiratory cycle phases. PID 13 can be coupled to system 10 and integrated into system 10.

Figure 9:
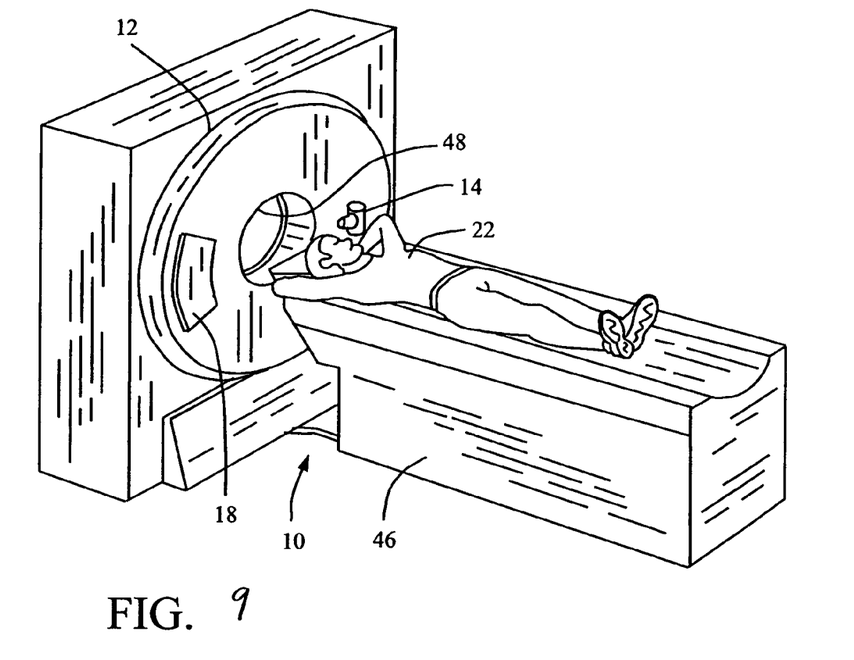
FIG. 9 is a pictorial view of a CT imaging system.
Figure 10:
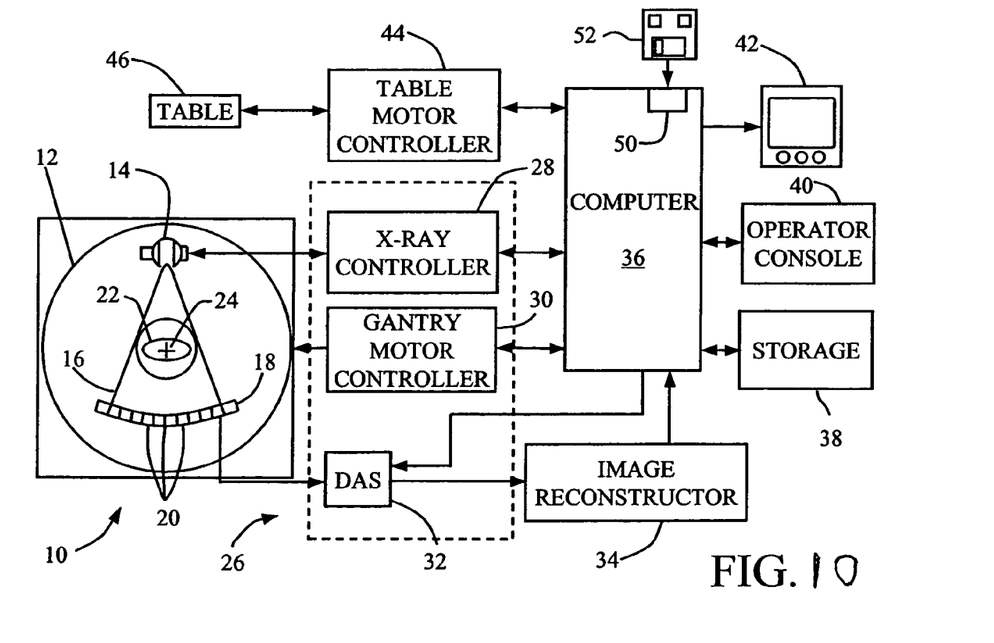
FIG. 10 is a block schematic diagram of the system illustrated in FIG. 9.

Referring to FIGS. 9 and 10, in one embodiment, imaging system 10 is a computed tomograph (CT) imaging system 10 including a gantry 12 representative of a "third generation" CT scanner. Gantry 12 has an x-ray source 14 that projects a beam of x-rays 16 toward a radiation detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam on that detector element and hence the attenuation of the beam as it passes through patient 22 at a corresponding angle. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. In one embodiment, console 40 is workstation 11. Computer 36 can be integrated with console 40 and can be remote from console 40. An associated display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device (not shown), for example, a floppy disk drive or CD-ROM drive, for reading instructions and/or data from a computer-readable medium (not shown), such as a floppy disk or CD-ROM. In another embodiment, computer 36 executes instructions stored in firmware (not shown). Computer 36 is programmed to perform functions described herein, but other programmable circuits can be likewise programmed. For example, in one embodiment, DAS 32 performs functions described herein. Accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits, and other devices which include a computer such as a workstation or console.

In one embodiment of the present invention, a user of CT system 10 selects an exam (i.e., a prescription image) containing a volume data set that represents the heart at a given phase, or multiple volume datasets that represent the heart at multiple phases. In an embodiment wherein the datasets are multi-phase axial cardiac datasets, the user is prompted to select a desired phase. For example, when the user selects diastole as the desired phase, an endocardial volume of the left ventricle at an end diastole phase is generated without further user intervention as illustrated in FIG. 2. And when the user selects systole as the desired phase, an endocardial volume of the left ventricle at an end systole phase is generated without further user intervention. A software program running in computer 36 is then launched by the operator using display 42 and console 40. This software accepts as input designations of the volume data sets selected by the user. In use, the user selects a prescription and a user interface then appears on display 42 in accordance with the workflow process illustrated in FIG. 2. The user has the ability to skip any view for which an image is not desired.

It will be seen that embodiments of the present invention automate workflow so a clinician's prescription will be accurate even without training. In the case of CT imaging, embodiments of the present invention allow a user to create a full four-dimensional (4D) data set that is well-suited to functional study of the heart and that can be used in conjunction with analysis software applications. In one embodiment, the 4D data set includes a three-dimensional image and a time component.

In addition, embodiments of the present invention are able to load CT images in a single phase of the heart or multiple phases at the same location. For example, a single phase data set can include image location S0 to I100 at 70% of the R to R interval. A multiphase data set might include image locations S0 to I100 at ten phases from 0 to 100% of the R to R interval. Data sets in one embodiment of the present invention have the same short/long axis plane throughout, thereby allowing a user to observe wall motion, ejection fracture, wall thickness, and perfusion.

In MR applications, post-processing embodiments of the present invention may be used to create short and long axis views. One post-processing embodiment of the present invention utilizes data obtained from MR, but utilizes software running on a computer separate from the MR as well as a separate display and operator console. This embodiment reduces the scan prescription time. Cost is also reduced, because time on the operator console is more expensive than time at a workstation. Thus, clinical productivity (measured in MR patients scanned per day) is increased by this embodiment. In addition, embodiments of the present invention allow rescans to be avoided if prescriptions are not correct.

The methods and systems described herein eliminate inter and intra user variation dependencies and streamlines the process of calculating LV functional parameters. As the volume measurements exclude both the contribution of papillary muscles and smoothing of the contours of the LV, the resulting ejection fraction is a true representation of the cardiac function even in patients with diseased ventricles. Technical effects of the herein described methods and apparatus include an improved accuracy of cardiac functional parameters, an increased reproducibility, a streamlined workflow via automated processes (less manual steps), and a higher productivity. Additionally, the herein described methods and apparatus do not rely on highly trained physicians, reduce the number of images created by removing a manual short axis image creation step, and by generating one less set of images, less disk space of the system is used. Also, the herein described methods are portable over multiple operating environments.

While the invention has been described in terms of various specific embodiments, those skilled in the art will recognize that the invention can be practiced with modification within the spirit and scope of the claims.

What is claimed is:

1. A method for generating views of a heart, said method comprising:
    scanning a patient's heart using an imaging scanner to generate a multi-phase axial cardiac dataset;
    transferring the multi-phase axial cardiac dataset to a computer;
    receiving a selection of a heart phase from a user at the computer, said selection comprising at least one of a systole phase and a diastole phase;
    segmenting a left cavity volume image of the heart from the multi-phase axial cardiac dataset;
    calculating an axis of inertia of the segmented left cavity volume image;
    automatically generating, based on the calculated axis of inertia, at least one of a long axis orientation image and a short axis orientation image of the heart; and
    generating an endocardial volume of a left ventricle at an end of the selected phase without further user intervention, wherein the generated volume excludes a plurality of papillary muscles.

2. A method in accordance with claim 1 wherein said transferring the multi-phase axial cardiac dataset to a computer comprises receiving, at the computer, a computed tomography (CT) multi-phase axial cardiac dataset.

3. A method in accordance with claim 1 wherein said transferring the multi-phase axial cardiac dataset to a computer comprises receiving, at the computer, a positron emission tomography (PET) multi-phase axial cardiac dataset.

4. A method in accordance with claim 1 wherein said transferring the multi-phase axial cardiac dataset to a computer comprises receiving, at the computer, a magnetic resonance (MR) multi-phase axial cardiac dataset.

5. A method in accordance with claim 1 wherein said generating an endocardial volume of a left ventricle at an end of the selected phase without further user intervention comprises generating an endocardial volume of a left ventricle at an end systole phase without user intervention by using at least one of a thresholding tool, a morphological tool, a connectivity tool, an edge detection tool, and a region growing tool.

6. A method in accordance with claim 5 wherein said generating an endocardial volume of a left ventricle at an end systole phase without user intervention by using at least one of a thresholding tool, a morphological tool, a connectivity tool, an edge detection tool, and a region growing tool comprises using said tools such that a contour of a slice is not smoothed.

7. A method in accordance with claim 5 wherein said generating an endocardial volume of a left ventricle at an end systole phase without user intervention by using at least one of a thresholding tool, a morphological tool, a connectivity tool, an edge detection tool, and a region growing tool comprises:
    generating an endocardial volume of a left ventricle at an end systole phase without user intervention by using a thresholding tool, an edge detection tool, and a region growing tool;
    using at least one of a thresholding tool, a morphological tool, a connectivity tool, an edge detection tool, and a region growing tool to segment a contrast within the generated endocardial volume of the left ventricle at the end systole phase from myocardium to volume render the contrast contained within the left ventricle at the end systole phase to generate a contrast segmented endocardial volume of the left ventricle at the end systole phase; and
    measuring the contrast segmented endocardial volume of the left ventricle at the end systole phase.

8. A method in accordance with claim 7 further comprising:
    providing the contrast segmented endocardial volume of the left ventricle at the end systole phase to a user for at least one of a verification and an edition of said myocardial contour of the volume prior to said measuring;
    receiving at least one of an indication of verification by the user and an edit from the user; and
    measuring the contrast segmented endocardial volume of the left ventricle at the end systole phase to calculate at least one of an end diastolic volume, an end systolic volume, an ejection fraction, a stroke volume, and a cardiac output without further user intervention.

9. A method in accordance with claim 1 further comprising:
    providing the generated volume to a user for at least one of a verification and an edition of a myocardial contour for the volume;
    receiving at least one of an indication of verification by the user and an edit from the user; and
    calculating at least one of an end diastolic volume, an end systolic volume, an ejection fraction, a stroke volume, and a cardiac output using a generated endocardial volume of the left ventricle at an end systole phase and a generated endocardial volume of the left ventricle at an end diastole phase without further user intervention.

10. A method in accordance with claim 1 further comprising calculating an end diastolic volume, an end systolic volume, an ejection fraction, a stroke volume, and a cardiac output using a generated endocardial volume of the left ventricle at an end systole phase and a generated endocardial volume of the left ventricle at an end diastole phase without user intervention.

11. A medical imaging apparatus for generating views of a heart along anatomically useful planes, said medical imaging apparatus comprising:
    an imaging system comprising:
    a detector array;
    at least one radiation source;
    a computer coupled to said detector array; and
    a workstation coupled to said computer, said workstation configured to:
        receive a multi-phase axial cardiac dataset from said computer;
        receive a selection of a heart phase from a user;
        segment a left cavity volume image of the heart from said multi-phase axial cardiac dataset;
        calculate an axis of inertia of said segmented left cavity volume image; and
        automatically generate, based on said calculated axis of inertia, at least one of a long axis orientation image and a short axis orientation image of the heart; and
        generate an endocardial volume of a left ventricle at an end of the selected phase without further user intervention, wherein the generated volume excludes a plurality of papillary muscles.

12. An apparatus in accordance with claim 11 wherein said imaging system further comprises a Positron Emission Tomography (PET) system and said at least one radiation source comprises an emission radiation source.

13. An apparatus in accordance with claim 11 wherein said imaging system further comprises a Computed Tomography (CT) system, said at least one radiation source comprises a transmission radiation source, and said computer is communicatively coupled to said transmission radiation source.

14. An apparatus in accordance with claim 11 wherein said workstation is further configured to calculate at least one of an end diastolic volume, an end systolic volume, an ejection fraction, a stroke volume, and a cardiac output using a generated endocardial volume of the left ventricle at an end systole phase and a generated endocardial volume of the left ventricle at an end diastole phase.

15. An apparatus in accordance with claim 14 wherein said workstation is further configured to:
provide the generated volumes to a user for at least one of a verification and an edition of a myocardial contour for each of the volumes;
receive at least one of an indication of verification by the user and an edit from the user; and
calculate at least one of an end diastolic volume, an end systolic volume, an ejection fraction, a stroke volume, and a cardiac output using the generated endocardial volume of the left ventricle at the end systole phase and the generated endocardial volume of the left ventricle at the end diastole phase without further user intervention.

16. An apparatus in accordance with claim 11 wherein said workstation is further configured to:
generate the endocardial volume of the left ventricle at an end systole phase and an end diastole phase without user intervention by using a thresholding tool, an edge detection tool, and a region growing tool;
use at least one of a thresholding tool, a morphological tool, a connectivity tool, an edge detection tool, and a region growing tool to segment a contrast within the generated endocardial volume of the left ventricle at the end systole phase and the end diastole phase from myocardium to volume render the contrast contained within the left ventricle at the end systole phase and the end diastole phase to generate a contrast segmented endocardial volume of the left ventricle at the end systole phase and a contrast segmented endocardial volume of the left ventricle at the end diastole phase; and
measure the contrast segmented endocardial volume of the left ventricle at the end systole phase and the contrast segmented endocardial volume of the left ventricle at the end diastole phase.

17. A combination comprising:
a computer; and
a computer readable medium encoded with a program executable by the computer for generating views of a heart along anatomically useful planes, said program configured to instruct the computer to:
receive a multi-phase axial cardiac dataset of the heart;
receive a selection of a phase;
segment a left cavity volume image of the heart from said multi-phase axial cardiac dataset;
calculate an axis of inertia of said segmented left cavity volume image;
automatically generate, based on said calculated axis of inertia, at least one of a long axis orientation and a short axis orientation image of the heart;
generate an endocardial volume of a left ventricle at an end systole phase without further input;
generate an endocardial volume of the left ventricle at an end diastole phase without further input;
provide the generated volumes to a user for at least one of a verification and an edition of a myocardial contour for the volumes, wherein the generated volumes exclude a plurality of papillary muscles; and
receive at least one of an indication of verification by the user and an edit from the user.

18. A combination in accordance with claim 17 wherein said program is further configured to instruct the computer to calculate at least one of an end diastolic volume, an end systolic volume, an ejection fraction, a stroke volume, and a cardiac output using the generated endocardial volume of the left ventricle at the end systole phase and the generated endocardial volume of the left ventricle at the end diastole phase.

* * * * *